(12) United States Patent
Isaacson et al.

(10) Patent No.: US 7,722,563 B2
(45) Date of Patent: May 25, 2010

(54) VASCULAR ACCESS DEVICE STAGNANT FLUID DISPLACEMENT

(75) Inventors: S. Ray Isaacson, Roy, UT (US); Bryan G. Davis, Sandy, UT (US); Dinesh S. Kommireddy, Tarrytown, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 176 days.

(21) Appl. No.: 11/866,825

(22) Filed: Oct. 3, 2007

(65) Prior Publication Data

US 2008/0086100 A1 Apr. 10, 2008

Related U.S. Application Data

(60) Provisional application No. 60/828,353, filed on Oct. 5, 2006.

(51) Int. Cl.
*A61M 37/00* (2006.01)
*A61M 5/178* (2006.01)
*A61M 5/24* (2006.01)
*A61M 5/28* (2006.01)

(52) U.S. Cl. .................... 604/86; 604/167.03; 604/201; 604/288.02

(58) Field of Classification Search .................... 604/83, 604/86, 167.02–167.04, 201, 284, 288.02–288.04, 604/533, 539
See application file for complete search history.

(56) References Cited

U.S. PATENT DOCUMENTS

| 4,765,588 | A | 8/1988 | Atkinson |
|---|---|---|---|
| 4,929,236 | A | 5/1990 | Sampson |
| 5,108,380 | A | 4/1992 | Herlitze et al. |
| 5,188,607 | A | 2/1993 | Wu |
| 5,251,873 | A | 10/1993 | Atkinson et al. |
| 5,295,657 | A | 3/1994 | Atkinson |
| 5,295,658 | A | 3/1994 | Atkinson et al. |
| 5,322,518 | A | 6/1994 | Schneider et al. |
| 5,342,316 | A | 8/1994 | Wallace |
| 5,441,487 | A | 8/1995 | Vedder |
| 5,474,544 | A | 12/1995 | Lynn |
| 5,501,426 | A | 3/1996 | Atkinson et al. |
| 5,533,708 | A | 7/1996 | Atkinson et al. |
| 5,549,651 | A | 8/1996 | Lynn |
| 5,699,821 | A | 12/1997 | Paradis |
| 5,957,898 | A | 9/1999 | Jepson et al. |
| 6,050,978 | A | 4/2000 | Orr et al. |
| 6,089,541 | A | 7/2000 | Weinheimer et al. |
| 6,171,287 | B1 | 1/2001 | Lynn et al. |
| 6,261,282 | B1 | 7/2001 | Jepson et al. |
| RE37,357 | E | 9/2001 | Lynn |
| 6,344,033 | B1 | 2/2002 | Jepson et al. |
| 6,595,964 | B2 | 7/2003 | Finley et al. |

(Continued)

*Primary Examiner*—Nicholas D Lucchesi
*Assistant Examiner*—Rebecca E Eisenberg
(74) *Attorney, Agent, or Firm*—Mony R. Ghose; Craig Metcalf; Kirton & McConkie

(57) ABSTRACT

A medical device may include an extravascular system, a vascular access device attached to the system, and at least one access port attached to the device capable of displacing stagnant fluid within the extravascular system. A method for eliminating stagnant fluid within an extravascular system may include providing an extravascular system, providing a vascular access device having an access port, attaching the device to the system via the access port, accessing the access port with a separate vascular access device, and displacing stagnant fluid within the extravascular system.

18 Claims, 8 Drawing Sheets

U.S. PATENT DOCUMENTS

| | | |
|---|---|---|
| 6,651,956 B2 | 11/2003 | Miller |
| 6,669,681 B2 | 12/2003 | Jepson et al. |
| 6,866,656 B2 | 3/2005 | Tingey et al. |
| 6,908,459 B2 | 6/2005 | Harding et al. |
| 2001/0020153 A1* | 9/2001 | Howell .................. 604/167.04 |
| 2002/0193752 A1 | 12/2002 | Lynn |
| 2005/0256500 A1 | 11/2005 | Fujii |
| 2006/0058744 A1* | 3/2006 | Tallarida et al. ........ 604/288.04 |

* cited by examiner

VASCULAR ACCESS DEVICE STAGNANT FLUID DISPLACEMENT

RELATED APPLICATIONS

This application claims the benefit of U.S. Provisional Application No. 60/828,353, filed Oct. 5, 2006, entitled VASCULAR ACCESS DEVICE STAGNANT FLUID DISPLACEMENT, which is incorporated herein by reference.

BACKGROUND OF THE INVENTION

The present disclosure relates to the elimination of stagnant flow in extravascular systems used to provide infusion or other therapy to patients. Infusion therapy is one of the most common health care procedures. Hospitalized and home care patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by vascular access devices located outside the vascular system of a patient. An extravascular system includes least one vascular access device and/or other medical device that may access a patient's peripheral or central vasculature, either directly or indirectly. Vascular access devices include closed access devices, such as the BD Q-SYTE™ closed Luer access device of Becton, Dickinson and Company; syringes; split access devices; catheters; and intravenous (IV) fluid chambers. An extravascular system may access a patient's vascular system for a short term (days), a moderate term (weeks), or a long term (months to years), and may be used for continuous infusion therapy or for intermittent therapy.

Complications associated with infusion therapy include significant morbidity and even mortality. Such complications may be caused by regions of stagnant flow within the vascular access device or nearby areas of the extravascular system. These are regions in which the flow of fluid is limited or non-existent due to the conformation of the extravascular system or the fluid dynamics within that area of the extravascular system. Air bubbles or infused medications may become trapped within these regions of stagnant flow as a result of the limited or non-existent fluid flow. When a different medication is infused into the extravascular system, or the extravascular system is exposed to physical trauma, the extravascular system's fluid flow may become altered, releasing trapped air bubbles or residual medications back into the active fluid path of the extravascular system. This release of air bubbles and residual medication into the active fluid path extravascular system may result in significant complications.

Released air bubbles may block fluid flow through the extravascular system and prevent its proper functioning. More seriously, released air bubbles may enter the vascular system of the patient and block blood flow, causing tissue damage and even stroke. In addition, residual medications may interact with presently infused medications to cause precipitates within the extravascular system and prevent its proper functioning. Furthermore, residual medications may enter the vascular system of the patient and cause unintended and/or undesired effects.

Therefore, a need exists for systems and methods that eliminate, prevent, or limit regions of stagnant flow within vascular access devices and extravascular systems.

BRIEF SUMMARY OF THE INVENTION

The present invention has been developed in response to problems and needs in the art that have not yet been fully resolved by currently available extravascular systems, devices, and methods. Thus, these developed systems, devices, and methods provide an extravascular system that may be connected to a patient's vascular system and will eliminate, prevent, or limit regions of stagnant flow within the vascular access device or the extravascular system.

A medical device for eliminating stagnant fluid within an extravascular system may include an extravascular system, a vascular access device attached to the extravascular system, and at least one access port attached to the vascular access device. The access port may displace stagnant fluid within the extravascular system. The access port may include a cam valve. The cam valve may be spring-loaded. The cam valve may open upon access of the access port, causing the cam valve to receive fluid. The cam valve may close upon removal of a separate vascular access device from the access port, causing the cam valve to expel fluid.

The medical device may also include an active fluid path within the extravascular system. The access port may be in direct contact with the active fluid path. The medical device may also include an extensible housing of the extravascular system, and the access port may be secured to the extensible housing. The extensible housing may be elastic. The medical device may also include a positive stop within the active fluid path of the extravascular system and opposite the access port. The extensible housing may extend when a separate vascular access device accesses the access port and exerts force against the positive stop.

The access port may be at an obtuse angle in relation to the fluid path downstream from the access port. The access port may include a septum having a convex bottom surface in contact with the active fluid path.

A method for eliminating stagnant fluid within an extravascular system may include providing an extravascular system, providing a vascular access device having an access port, attaching the vascular access device to the extravascular system via the access port, accessing the access port with a separate vascular access device, and displacing stagnant fluid within the extravascular system. The access port may include a cam valve and the method may further include opening the cam valve. The method may further include closing the cam valve.

The extravascular system may include an active fluid path and the method may include placing the access port in direct contact with the active fluid path. The extravascular system may include an extensible housing and the method may include attaching the access port to the extensible housing and, upon accessing the access port, extending the extensible housing.

Attaching the vascular access device to the extravascular system may include setting the access port at an angle that is obtuse from the fluid path downstream of the access port. The method may include adding material to the access port to replace space where the stagnant fluid would reside within the extravascular system absent the added material.

A medical device may include a means for accessing the vascular system of a patient and a means for displacing stagnant fluid. The means for displacing stagnant fluid may reside within the means for accessing the vascular system of the patient.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
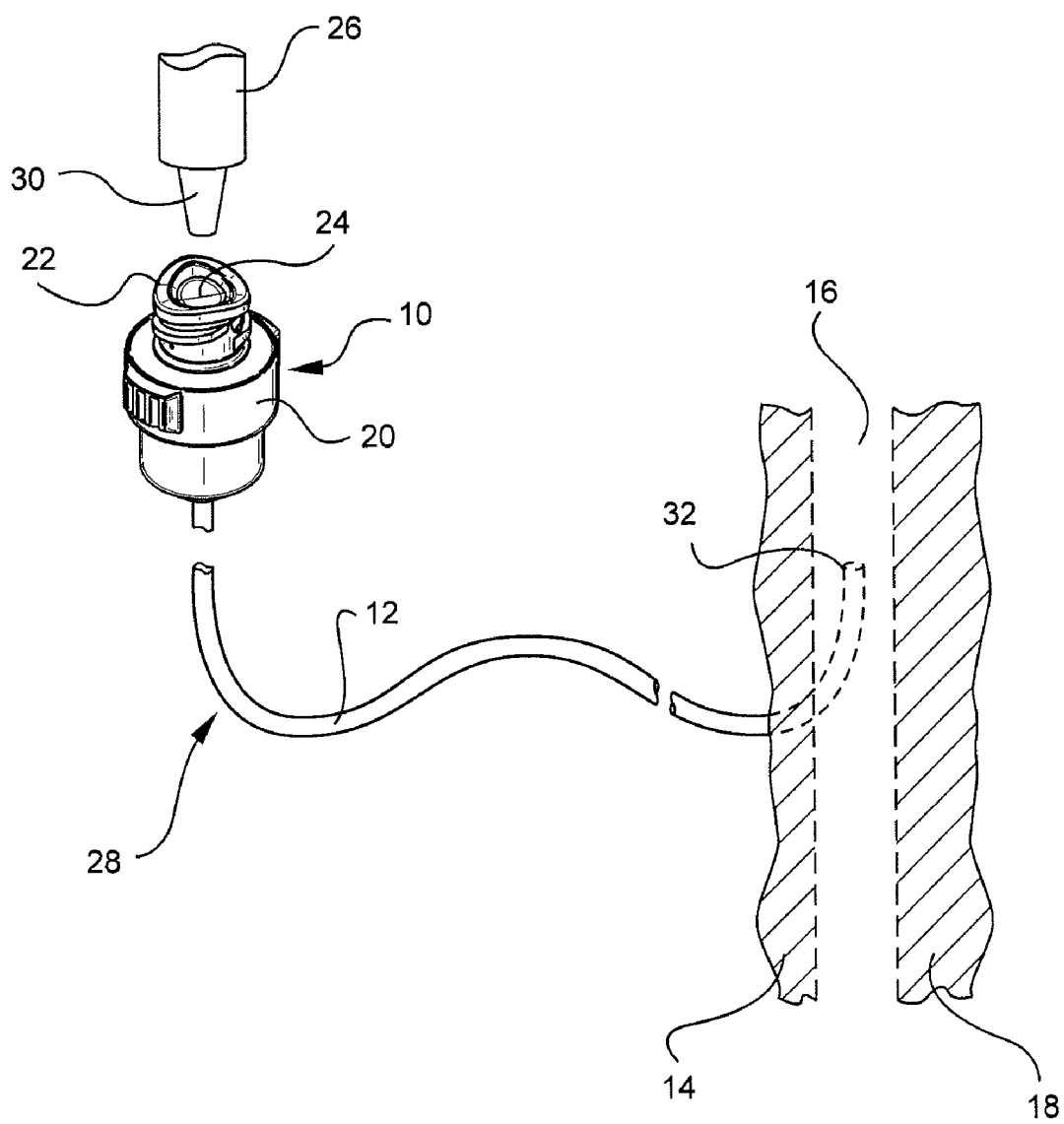
FIG. 1 is a perspective view of an extravascular system connected to the vascular system of a patient.

Referring now to FIG. 1, a vascular access device 10 is used to introduce a substance along a fluid path via a catheter 12 across the skin 14 and into a blood vessel 16 of a patient 18. The vascular access device 10 includes a body 20 and an access port 22. The access port 22 has a slit septum 24 through which a separate vascular access device 26 having a tip 30, such as a syringe, may introduce a substance into the vascular access device 10. The vascular access device 10 (also referred to as an extravascular device, intravenous access device, and/or any device attached to or functioning with an extravascular system) and the separate vascular access device 26 form at least part of an extravascular system 28. The vascular access device 10 may be secured to an adapter, a catheter 12, or any other extravascular device at any attachment location and in any attachment orientation.

Figure 2:
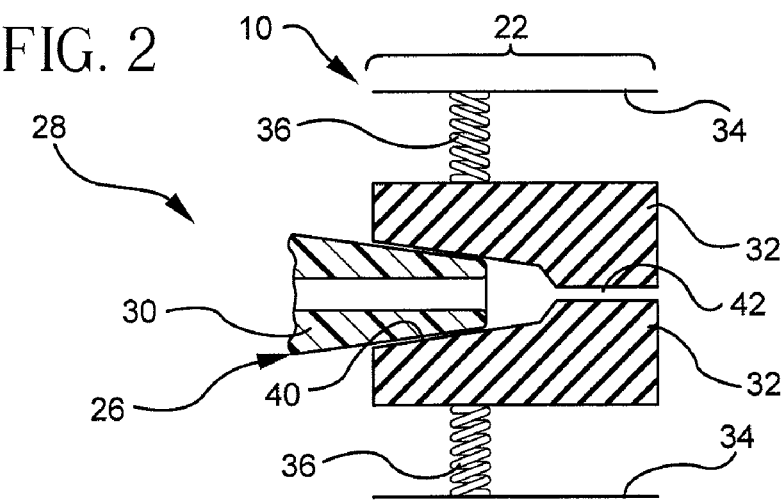
FIG. 2 is a partial cross section view of a separate vascular access device accessing an access port.

Referring now to FIG. 2, a partial cross section view of a vascular access device 10 and a separate vascular access device 26 of an extravascular system 28 shows the tip 30 of the separate vascular access device 26 being inserted into the access port 22 of the vascular access device 10. The access port 22 includes two separable halves 32, each independently secured to an inner wall 34 of the device 10 by means of separate compression springs 36. The two halves 32, under the compression of the springs 36 form a spring-loaded cam valve.

Each of the spring-loaded halves 32 includes a tapered inner surface 40 capable of communicating with an outer surface of the tip 30 such that the tip 30 causes the two halves 32 to separate as the tip 30 is advanced into the access port 22 and against the two tapered surfaces 40. Thus, the cam valve of the access port 22 opens as the access port 22 is accessed by a separate vascular access device 26. As the cam valve opens, a fluid path 42 opens and widens between the two halves 32.

Figure 3:
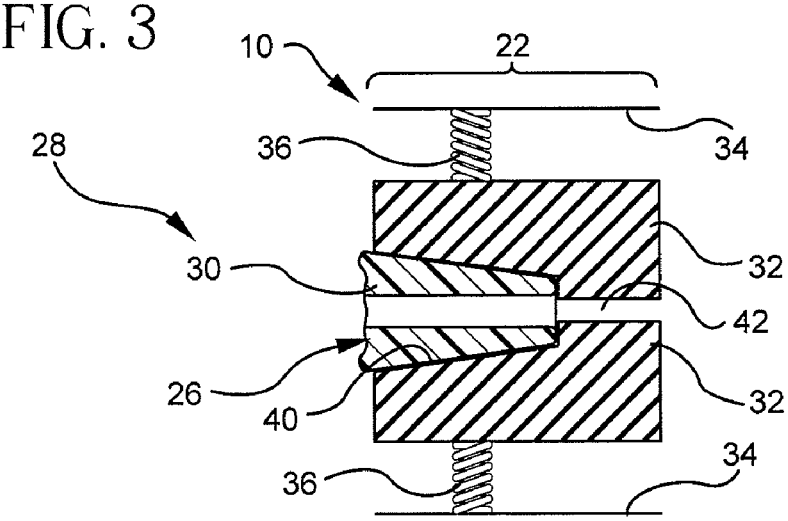
FIG. 3 is a partial cross section view of the separate vascular access device fully engaged with the access port of FIG. 2.

Referring now to FIG. 3, a partial cross section view of the embodiment described with reference to FIG. 2 is shown. As shown in FIG. 3, the tip 30 is fully advanced into the access port 22 and against the tapered inner surfaces 40, causing the two halves 32 to be compressed against their respective springs 36, and causing the fluid path 42 to be opened to its maximum width.

Figure 4:
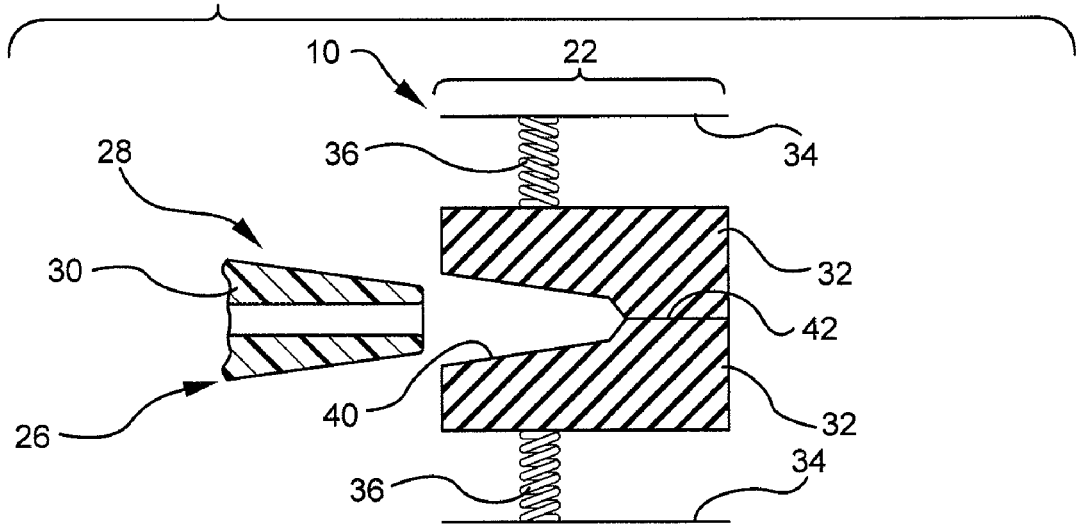
FIG. 4 is a partial cross section view of the separate vascular access device removed from the access port of FIG. 2.

Referring now to FIG. 4, the embodiment described with reference to FIGS. 2 and 3 is shown with the tip 30 of the separate vascular access device 26 removed from the access port 22. With the tip 30 removed from the access port 22, the compression springs 36 have forced the separate halves 32 to come into contact with each other, eliminating or closing the fluid path 42.

Figure 5:
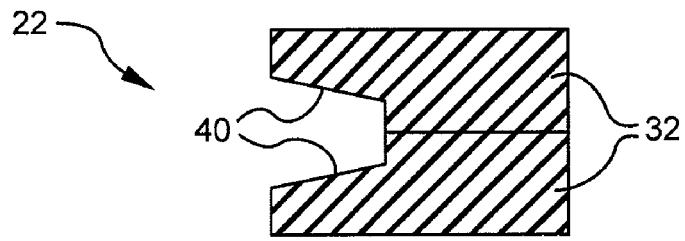
FIG. 5 is a cross section view of a closed cam valve.
Figure 6:
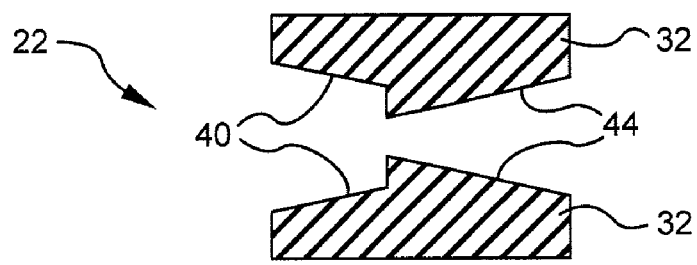
FIG. 6 is a cross section view of an open cam valve.

Referring now to FIGS. 5 through 8, a possible valve geometry of the cam valve described with reference to FIGS. 2 through 4 is shown and described. Referring first to FIG. 5, the cam valve of the access port 22 includes the two halves 32 in contact with each other. Referring now to FIG. 6, when the cam valve of the access port 22 is open, the separate halves 32 are separated from and not in contact with each other. In addition to the tapered inner surfaces 40 of the halves 32, the halves 32 include another tapered surface 44 on the interior surfaces of the halves 32. The other tapered surfaces 44 taper in a direction opposite the tapered surfaces 40. The material of the halves 32 may be pliable, such that the material may be compressed as the other tapered surfaces 44 come into contact with each other.

Figure 7:
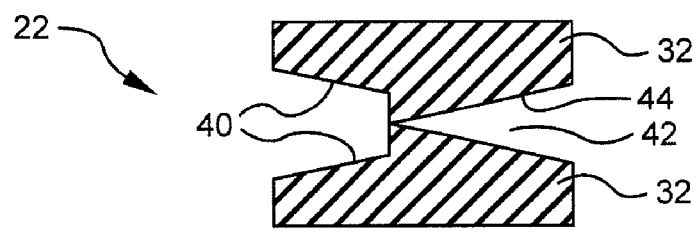
FIG. 7 is a cross section view of a closing cam valve.

Referring now to FIG. 7, the cam valve of the access port 22 is shown, beginning to close. The other inner surfaces 44 of the two halves 32 have begun to come into contact with each other. As the other tapered inner surfaces 44 come into contact with each other, the external environment 46 in which the extravascular system is placed is isolated from the fluid path 42 of the system 28. As the other tapered inner surfaces 44 isolate the external environment 46 from the fluid path 42, the fluid within the fluid path 42 may not exit the fluid path 42 towards the external environment 46.

Figure 8:
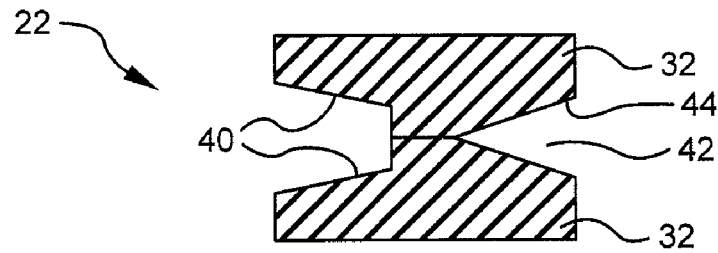
FIG. 8 is a cross section view of a cam valve that is closed further than the cam valve of FIG. 7.

Referring now to FIG. 8, the cam valve of the access port 22 described with reference to FIGS. 5 through 7 is shown with the two halves 32 further compressing towards one another. As the two halves 32 compress the material of each of the two halves 32 and come into further contact with each other, the other tapered inner surfaces 44 come into progressive contact with each other, forcing fluid within the fluid path 42 in a direction 48 away from the external environment 46 and into the extravascular system 28. Thus, the tapered inner surfaces 44 of the compressible halves 32 enable the cam valve to close upon removal of a separate vascular access device 26 from the access port 22, simultaneously causing the cam valve to expel fluid. The cam driven valve also advantageously eliminates space that would otherwise harbor stagnant fluid adjacent to the access port 22.

Figure 9:
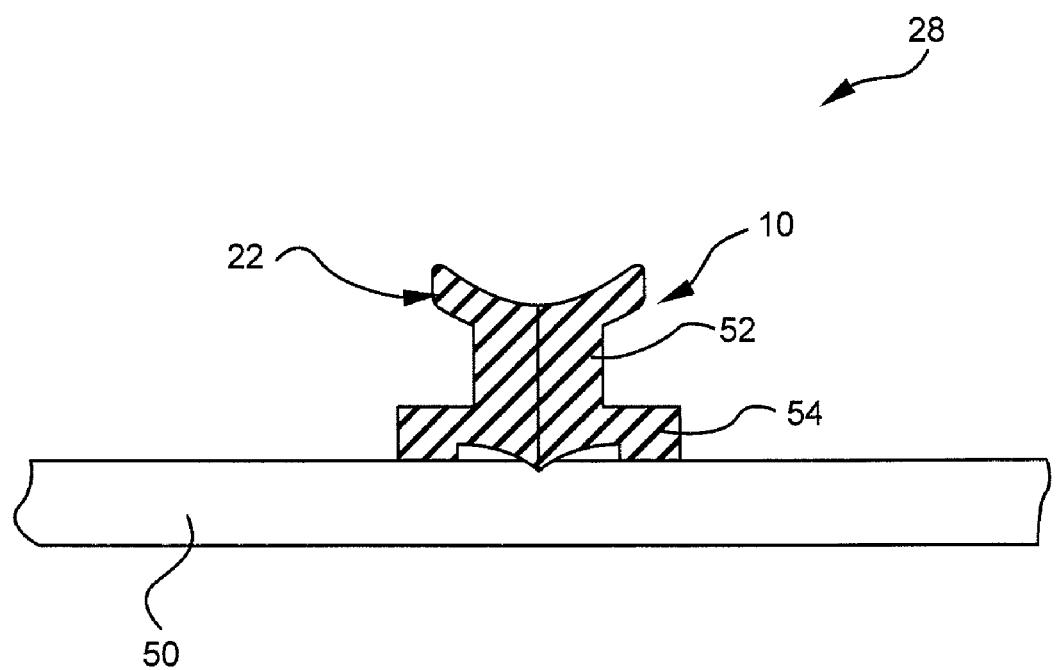
FIG. 9 is a cross section view of an access port in direct contact with an active fluid path.

Referring now to FIG. 9, an extravascular system 28 may include a vascular access device 10 attached to the extravascular system 28 and at least one access port 22 attached to the vascular access device 10. The access port 22 is in direct contact with the active fluid path 50 of the extravascular system 28. The access port 22 includes a septum 52 having a bottom disc 54 in contact with the active fluid path 50. The bottom disc 54 opens into the active fluid path 50 when the access port 22 is accessed by a separate vascular access device 26. However, since the length of the two halves 32 of the bottom disc 54 of the septum 52 is longer than the diameter of the active fluid path 50, the bottom disc 54 of the septum 52 may not fully open during access. Thus, an alternate embodiment, providing full access yet direct proximity or contact to the active fluid path 50, may be preferred and is described with reference to FIGS. 10 and 11.

Figure 10:
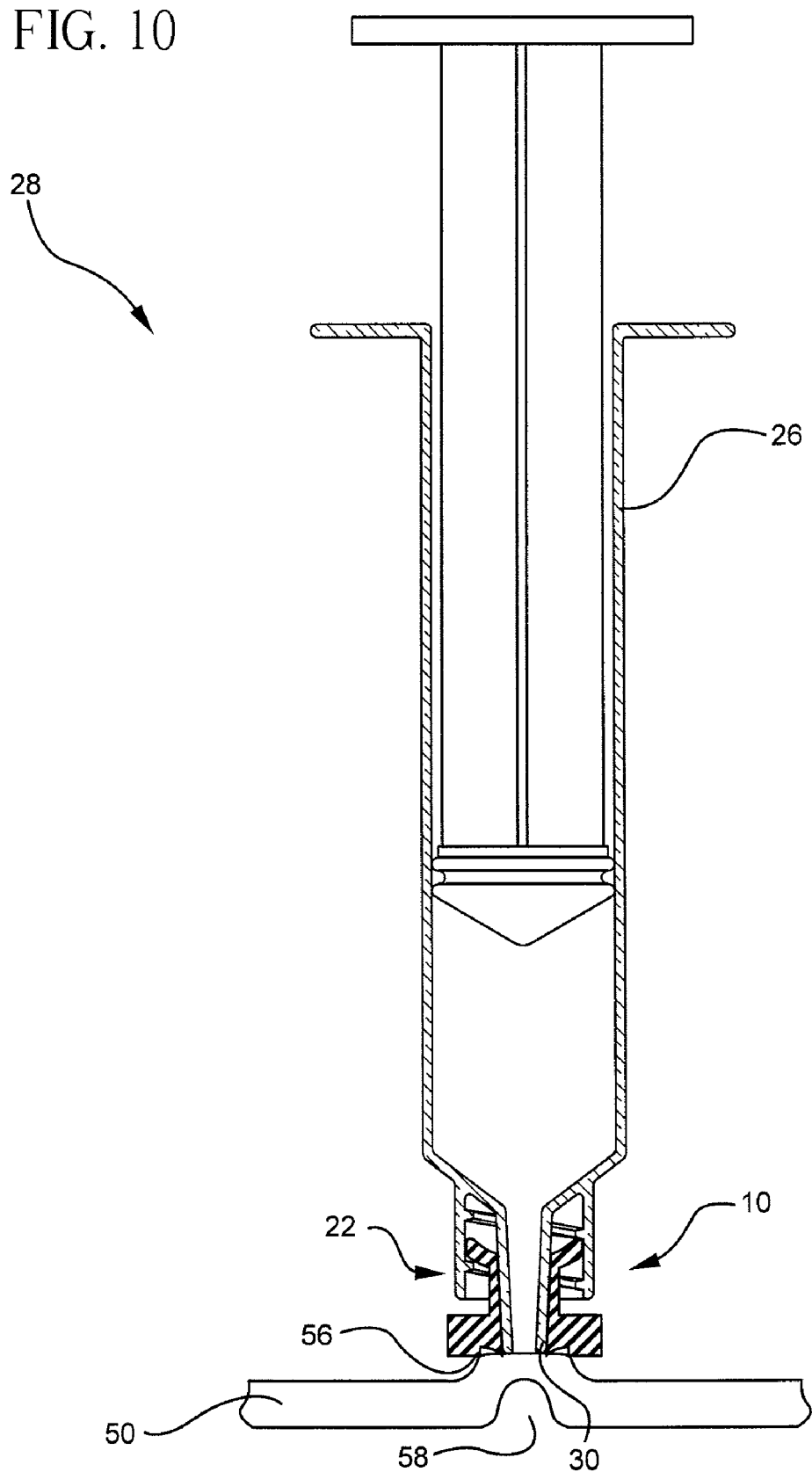
FIG. 10 is a cross section view of an access port secured to an extensible housing and in direct contact with an active fluid path.

Referring now to FIG. 10, an extravascular system 28 may include a separate vascular access device 26 secured to a vascular access device 10, which is in turn secured to a portion of the extravascular system having an extensible housing 56. The extensible housing 56 may be formed of elastic or other material capable of extending away from the active fluid path 50 of the system 28. The access port 22 of the device 10 is secured to the extensible housing 56.

The extravascular system 28 may also include a positive stop 58 within the active fluid path 50 of the extravascular system 28 and opposite the access port 22. When the tip 30 of a separate access device 26 is inserted into the access port 22, the tip 30 will ultimately come into contact with the positive stop 58. When the tip 30 comes into contact with and exerts force against the positive stop 58, the access port 22 may extend away from the active fluid path 50 by extending the extensible housing 56. The extensible housing 56 draws the access port 22 towards the tip 30 of the separate vascular access device 26 and extends when the separate vascular access device 26 accesses the access port 22 and exerts force against the positive stop 58.

The embodiment described with reference to FIG. 10 thus provides an extensible housing 56 that enables an access port 22 to be in direct contact with the active fluid path 50 of the system 28. In addition, the extensible housing 56 and positive stop 58 enable the tip 30 of a separate vascular access device 26 to be fully inserted and to be able to fully infuse into and operate within the active fluid path 50. Thus, the embodiment described with reference to FIG. 10 solves the limitations that exist in relation to the embodiment described with reference to FIG. 9.

Figure 11:
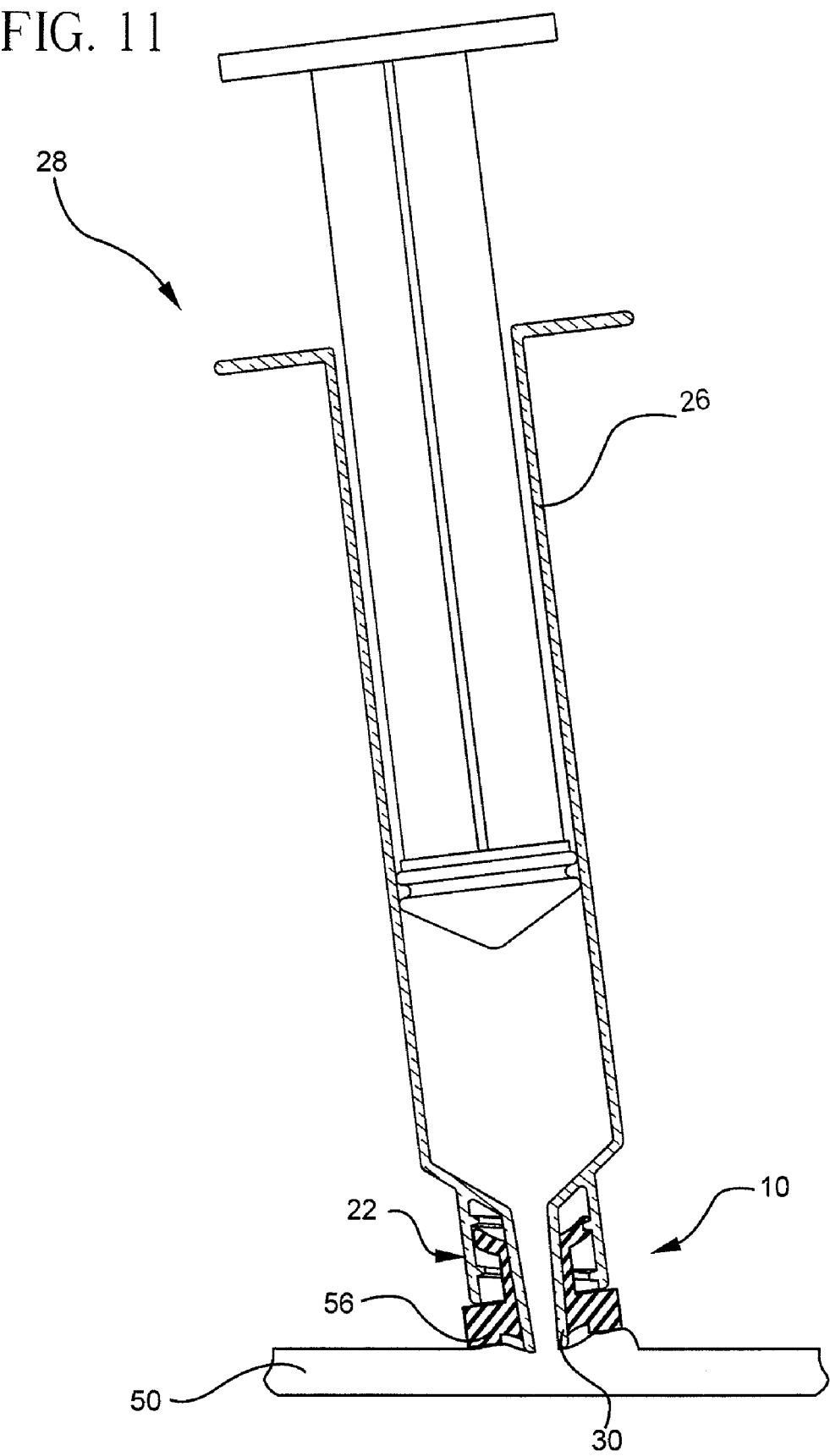
FIG. 11 is a cross section view of an access port at an obtuse angle to a downstream active fluid path.

Referring now to FIG. 11, an extravascular system 28 includes a separate vascular access device 26 inserted into a vascular access device 10 which is in turn connected or attached to a remaining portion of the extravascular system 28 having an active fluid path 50. The vascular access device 10 includes an access port 22. The access port 22 is in direct contact with the active fluid path 50. The access port 22 is at an angle that is obtuse, between 90 degrees and 180 degrees, in relation to the fluid path 50 that is downstream 60 from the access port 22. Thus, the embodiment described with reference to FIG. 11 enables the tip 30 of a separate access device 26 to be fully inserted at an obtuse angle into the access port 22 of the device 10 and into the active fluid path 50 of the system 28. When fully inserted, the tip 30 may function properly and fully infuse fluids into the active fluid path 50. Simultaneously, the bottom surface of the access port 22 is in direct contact with the active fluid path 50, eliminating or otherwise limiting any stagnant fluid that would otherwise exist between the active fluid path 50 and an access port 22 that was not in direct contact with the active fluid path 50.

The embodiments described with reference to FIGS. 9 through 11 thus provide access ports 22 in direct contact with the active fluid path 50 of an extravascular system 28. The embodiments described with reference to FIGS. 10 and 11 further provide access ports 22 capable of fully accepting the tips 30 of separate access devices 26 into the active fluid path 50. In addition, the embodiments described with reference to FIGS. 10 and 11 provide access ports 22 capable of displacing fluid into the active fluid path 50 as the separate vascular access devices 26 are removed from the access ports 22.

Figure 12:
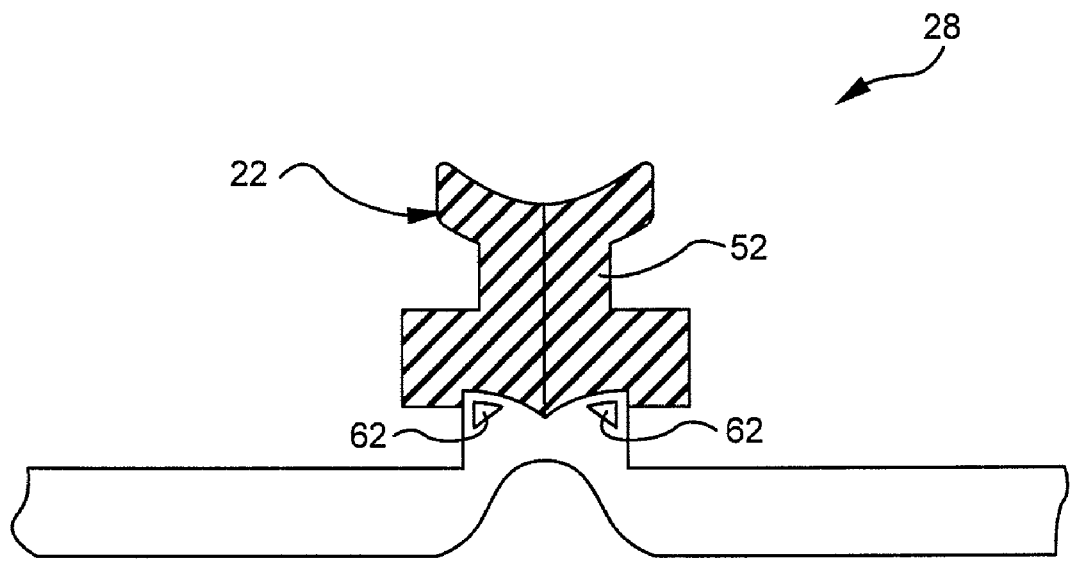
FIG. 12 is a cross section view of an access port in contact with stagnant fluid.

Referring now to FIG. 12, a traditional access port 22 of an extravascular system 28 includes a septum 52 with a concave bottom surface on the bottom disc 54 of the septum 52. The concave shape of the bottom surface of the bottom disc 54 provides an area of dead space 62 directly beneath the septum 52 where stagnant fluid may reside. Thus, an embodiment eliminating the dead space 62 may be preferred and will be described with reference to FIG. 13.

Figure 13:
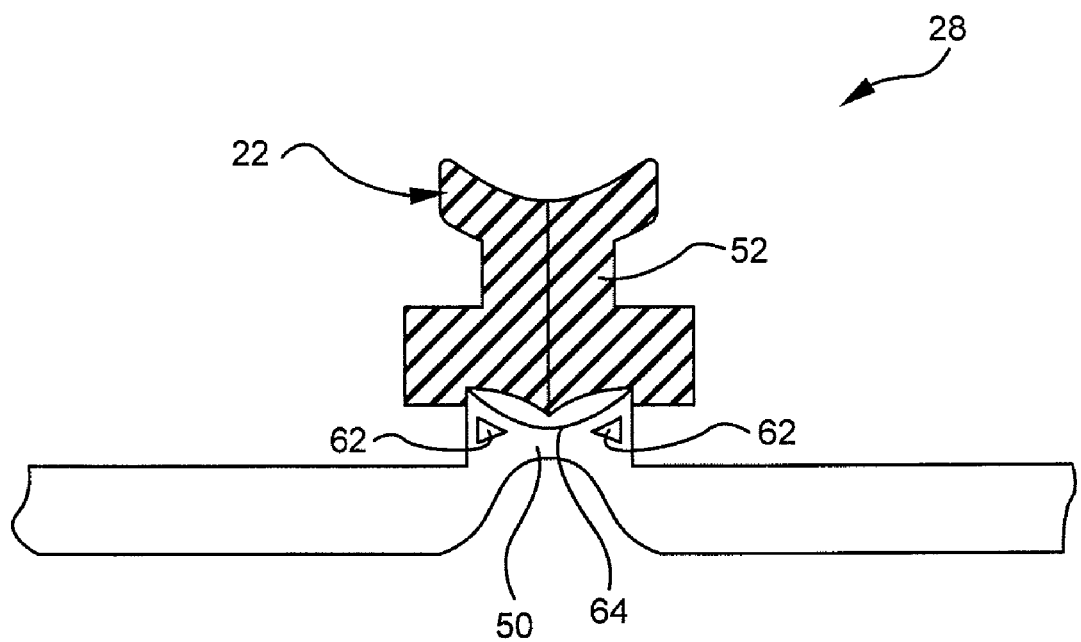
FIG. 13 is a cross section view of an access port with a concave surface in contact with an active fluid path.

Referring now to FIG. 13, an extravascular system 28 may include an access port 22 having a septum 52 with a convex bottom surface 64 in contact with the active fluid path 50 of the system 28. The convex bottom surface 64 protrudes into a space where dead space 62 is likely to harbor stagnant fluid. When the access port 22 is accessed by the tip 30 of a separate access device 26, the convex bottom surface 64 will open, protruding into the dead space 62 where the stagnant fluid resided prior to access. Thus, the embodiment described with reference to FIG. 13 provides an access port 22 with a convex bottom surface capable of eliminating or otherwise displacing dead space 62 where stagnant fluid may reside. The access ports 22 may reside closer to or more distant from the active fluid path 50.

Any of the features and elements described with reference to FIGS. 1 through 13 may be used in any combination and number in order to provide at least one access port capable of displacing, eliminating, limiting, or otherwise interacting with stagnant fluid within an extravascular system 28.

Figure 14:
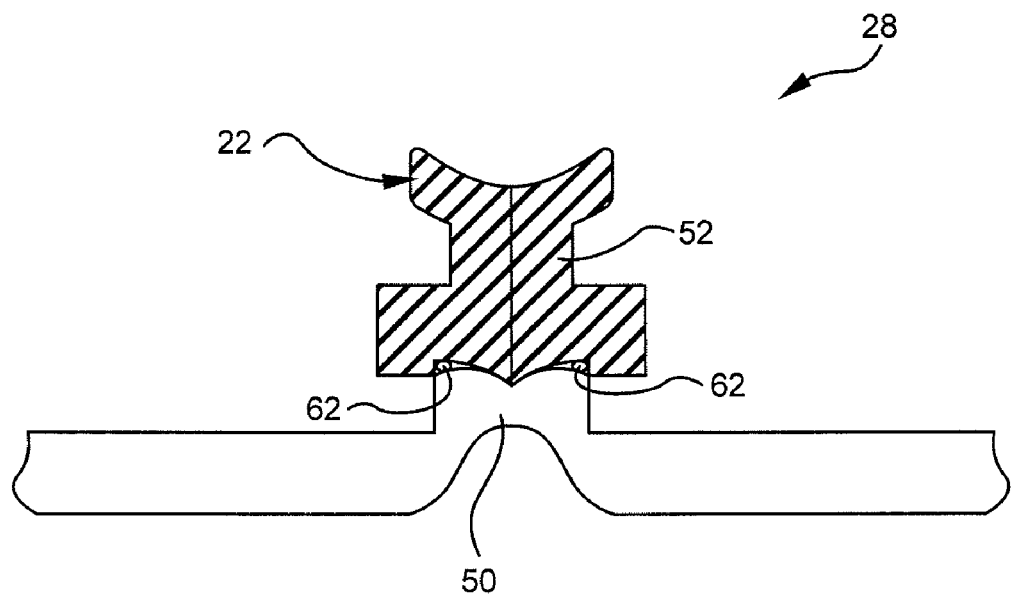
FIG. 14 is a cross section view of an access port of FIG. 13 being accessed by a separate vascular access device.
Figure 15:
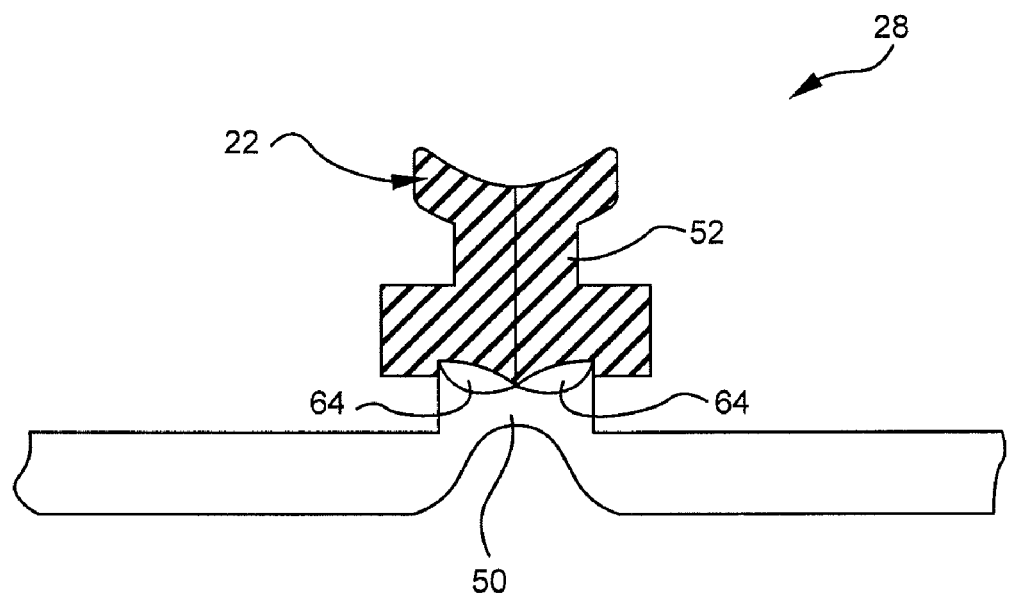
FIG. 15 is a cross section view of an access port having a projection to fill dead space.

FIGS. 14 and 15 illustrate the solution of a similar problem. FIG. 14 illustrates an access port 22 which may result in a dead space 62. As illustrated in FIG. 15, the dead space 62 is filled by two downward projections 64. Thus, the dead space 62 is occupied and will not result in the problems discussed above.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device for eliminating stagnant fluid within an extravascular system, comprising:
   an extravascular system;
   a vascular access device attached to the extravascular system; and
   at least one access port attached to the vascular access device, wherein access of the access port displaces stagnant fluid within the extravascular system, the access port comprising a cam valve, wherein the cam value includes two unattached halves, wherein each of the two unattached halves are compressed by separate springs, wherein each of the separate springs is coupled to one of the separable halves of the cam valve and to the housing.

2. The medical device of claim 1, wherein the two unattached halves open when a separate vascular access device is inserted into the valve.

3. The medical device of claim 2, wherein the cam valve closes when a separate vascular access device is removed from the access port, causing the cam valve to expel fluid.

4. The medical device of claim 1, further comprising an active fluid path within the extravascular system, wherein the cam valve is in direct contact with the active fluid path.

5. The medical device of claim 4, further comprising an extensible housing of the extravascular system, wherein the access port is secured to extensible housing.

6. The medical device of claim 5, further comprising a positive stop within the active fluid path of the extravascular system and opposite the cam valve.

7. The medical device of claim 6, wherein the extensible housing extends when a separate vascular access device accesses the cam valve and exerts force against the positive stop.

8. The medical device of claim 4, wherein the cam valve is at an obtuse angle in relation to the fluid path downstream from the cam valve.

9. The medical device of claim 4, wherein the cam valve includes a septum having a convex bottom surface in contact with the active fluid path.

10. The medical device of claim 1, wherein the separate springs are coil springs.

11. The medical device of claim 1, wherein each of the two separable halves of the cam valve includes an interior and exterior portion, and wherein the exterior portions of the two separable halves include a tapered surface.

12. The medical device of claim 11, wherein the interior portion of each of the two separable halves of the cam valve includes a tapered surface.

13. A medical device, comprising:
    a body;
    an access port providing fluid access to the interior of the body;
    a cam valve disposed within the body, the cam valve including two unattached halves, wherein each of the two unattached halves are compressed by a separate spring and wherein each of the separate springs is coupled to one of the separable halves of the cam valve and to the housing; and
    means for displacing stagnant fluid within the cam valve.

14. The medical device of claim 13, wherein each of the two separable halves of the cam valve includes an interior and exterior portion, and wherein the exterior portions of the two separable halves include a tapered surface.

15. The medical device of claim 14, wherein the interior portions of the two separable halves include a tapered surface.

16. A medical device for eliminating stagnant fluid within an extravascular system, comprising:
    an extravascular system having an extensible housing and a fluid path within the extravascular system;
    a vascular access device secured to the extensible housing of the extravascular system, wherein the vascular access device bisects the fluid path;
    an access port attached to the vascular access device wherein the access port is a cam valve having two separable halves each of which are compressed by a separate spring; wherein each of the separate springs is coupled to one of the separable halves of the cam valve and to the housing; and
    a positive stop within the active fluid path of the extravascular system and opposite the access port.

17. The medical device of claim 16, wherein the access port further includes a septum having a convex bottom surface in contact with the fluid path.

18. The medical device of claim 17, wherein the access port is at an obtuse angle in relation to the fluid path downstream from the access port.

* * * * *